United States Patent [19]

Sheperd

[11] Patent Number: 5,010,196

[45] Date of Patent: Apr. 23, 1991

[54] ACYLATED HEXAHYDROPYRIMIDINES

[75] Inventor: Robin G. Sheperd, Windsor, England

[73] Assignee: John Wyeth and Brothers Limited, Maidenhead, England

[21] Appl. No.: 591,594

[22] Filed: Oct. 2, 1990

Related U.S. Application Data

[62] Division of Ser. No. 544,452, Jun. 27, 1990.

[30] Foreign Application Priority Data

Jun. 30, 1989 [GB] United Kingdom ............ 8915131.0

[51] Int. Cl.⁵ .......................................... C07D 239/04
[52] U.S. Cl. ................................... 544/335; 544/242
[58] Field of Search ............................................ 544/335

[56] References Cited

U.S. PATENT DOCUMENTS

| | | | |
|---|---|---|---|
| 3,872,120 | 3/1975 | Mod et al. | 544/335 |
| 4,404,302 | 9/1983 | Gupta et al. | 544/335 |
| 4,404,379 | 9/1983 | Hajek et al. | 544/335 |
| 4,590,272 | 5/1986 | Shiowkawa et al. | 544/335 |
| 4,758,570 | 7/1988 | Harris et al. | 544/335 |

FOREIGN PATENT DOCUMENTS 0451698 10/1975 U.S.S.R. ............................ 544/335

OTHER PUBLICATIONS

Okada, J. et al., "N-Acetylation of 1,3-Diazines", CA 88, 89607 r (1978).
Schultz, A. et al., "Chemistry of Naturally Occurring Polyamines, etc.", *J. Org. Chem* 45, 2041-2042 (1980).
Chemical Abstracts 91: 125036b (1979).

*Primary Examiner*—Glennon H. Hollrah
*Assistant Examiner*—Susan P. Treanor
*Attorney, Agent, or Firm*—Richard K. Jackson

[57] ABSTRACT

N'-Acyl-N-alkyl-1,3-diaminopropanes of formula

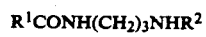

$R^1CONH(CH_2)_3NHR^2$ (where $R^1$ is R- or RNH where R is a substituted or unsubstituted hydrocarbon group and $R^2$ is alkyl) are prepared by selectively acylating N-alkyl-1,3-diaminopropanes. In the process a N-alkyl-1,3-aminopropane is reacted with an aldehyde to form a hexahydropyrimidine, the hexahydropyrimidine is acylated and the acylated hexahydropyrimidine is then hydrolyzed to give the product.

2 Claims, No Drawings

ACYLATED HEXAHYDROPYRIMIDINES

This is a division of application Ser. No. 07/544,452 filed June 27, 1990.

This invention relates to a process for preparing substituted 1,3-diaminopropanes and to intermediates useful in the process. In particular the invention relates to a process for selectively acylating N-alkyl-1,3-diaminopropanes to give N'-acyl-N-alkyl-1,3-diaminopropanes. In this specification "acyl" is to be understood to include both hydrocarbon acyl groups of the type RCO- and aminoacyl groups of the type RNHCO- (where R is a substituted or unsubstituted hydrocarbon group such as a substituted or unsubstituted alkyl or aryl group). "Acylating" is used in a similar manner as relating to the introduction of both types of "acyl" groups.

A number of N'-acyl-N-alkyl-1,3-diaminopropanes are described in the literature; compounds in which the acyl group is an aminoacyl group have been described as being useful as pharmaceuticals. For example, German Patent specification 1038031 discloses certain N-aminoalkyl-N'-(2-chloro-6-methylphenyl)-ureas as local anaesthetics. GB 2025406B discloses compounds of the formula

Y—NH.CONH.CH$_2$CH$_2$CH$_2$—NH—X (wherein Y is 2,6-dimethylphenyl, 2,5-dimethylphenyl, 5-bromo-2-methylphenyl or 5-chloro-2-methylphenyl and X is propyl, isopropyl, n-butyl or isobutyl) as being useful as anti-arrhythmic agents. A preferred compound is recainam which is the compound of the above formula in which Y is 2,6-dimethylphenyl and X is isopropyl.

The described processes for preparing the N'-acyl-N-alkyl-3-diaminopropanes have disadvantages especially when used on a commercial scale. For example reaction of an acylating agent with an N-alkyl-1,3-diaminopropane can give a mixture of products since the acylating agent can acylate either the primary or secondary amino group. GB 2025406B describes an alternative process in which the primary amino group in the starting material is protected but the yield is still poor because the process comprises a number of separate steps. A third method described in GB 2025406B involves reaction of, for example, a N-(3-chloropropyl)-N'-arylurea with an alkylamine. However the yield is poor and an impure product is obtained because of a side reaction in which the alkylamine reacts at the carbonyl group of the urea. A new process has now been found which gives the desired product by a short route in good yield.

Accordingly the present invention provides a process for preparing a N'-acyl-N-alkyl-1,3-diaminopropane of general formula (I)

R$^1$CONH(CH$_2$)$_3$NHR$^2$ (I)

(where R$^1$ is R- or R.NH- where R is a substituted or unsubstituted hydrocarbon group and R$^2$ is alkyl) which comprises reacting a diamine of formula (II)

NH$_2$(CH$_2$)$_3$NHR$^2$ (II)

(where R$^2$ has the meaning given above) with an aldehyde of formula (III)

R$^3$CHO (III)

(where R$^3$ represents hydrogen or lower alkyl to give a hexahydropyrimidine of formula (IV)

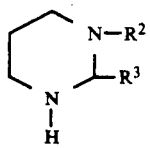

(IV)

(where R$^2$ and R$^3$ having the meanings given above), acylating the hexahydropyrimidine to give an acylated hexahydropyrimidine of formula (V)

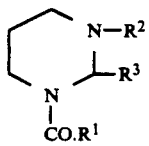

(V)

(where R$^1$, R$^2$ and R$^3$ have the meanings given above) and hydrolysing the acylated hexahydropyrimidine.

R is preferably a substituted or unsubstituted alkyl or aryl group. The alkyl group may, for example, be lower alkyl. The term "lower" as used herein means that the radical referred to contains 1 to 6 carbon atoms. Preferably such radicals contain 1 to 4 carbon atoms. Thus the R group may be, for example, methyl, ethyl, propyl or butyl. When R is an aryl group it is preferably a hydrocarbon aryl group containing 6 to 10 carbon atoms such as phenyl, alkylphenyl or naphthyl. The alkyl or aryl group may be substituted particularly by one or more substituents common in medicinal chemistry. Such substituents include halogen (for example, fluorine, chlorine, bromine), hydroxy, alkoxy (e.g. lower alkoxy groups such as methoxy, ethoxy, propoxy, butoxy) amino, monoalkylamino (e.g. lower alkylamino such as methylamino), dialkylamino (e.g. diloweralkylamino), acylamino (particularly lower acylamino e.g. acetamino) and trifluoromethyl. Preferably R$^1$ represents RNH- and preferably R is a substituted or unsubstituted phenyl group such as those given in the definition of Y above.

R$^2$ is preferably a lower alkyl group. Examples are given above in connection with the group R. Preferably R$^2$ is propyl, isopropyl, n-butyl or isobutyl as given in the definition of X above.

The most preferred compound of formula (I) is that in which R$^1$ represents RNH- where R is 2,6-dimethylphenyl and R$^2$ is isopropyl.

In the process of the invention the diamine of formula (II) is reacted with an aldehyde of formula (III). In formula (III), preferably R$^3$ is hydrogen, i.e. the aldehyde is formaldehyde. The reaction can be carried out in a solvent. Examples of solvents includes water, lower alkanols and aqueous lower alkanols.

It is not necessary to isolate the hexahydropyrimidine; the reaction product of the diamine and the aldehyde can be reacted in situ with an acylating agent in order to acylate the hexahydropyrimidine. When R$^1$ represents R.NH the acylating agent is preferably an isocyanate, particularly a substituted or unsubstituted aryl isocyanate. When R$^1$ represents R- the acylating agent may be any of the acylating agents known in the art such as acyl halides, acid anhydrides and the like.

Again it is not necessary to isolate the acylated hexahydropyrimidine. The reaction product of the acylation reaction can be hydrolysed in situ to the desired product. The hydrolysis can be carried out with water although in some instances (particularly when $R^3$ is hydrogen) it is preferable to use an aqueous solution of an alkaline metal bisulphite (e.g. sodium bisulphite) to combine with the aldehyde which is released.

It is an advantage of the process of the present invention that it is not necessary to isolate the intermediates of formula (IV) and (V) i.e. the whole process can be carried out in the same reaction vessel.

The products of formula (I) form acid addition salts and can be isolated in the form of the free base or in the form of a pharmaceutically acceptable acid addition salt prepared by reaction of the free base with a pharmaceutically acceptable organic or inorganic acid. Suitable acids will be apparent to those skilled in the art. Examples of such acids are p-toluene sulphonic (tosyl), hydrochloric and phosphoric. The tosyl and hydrochloric salts are generally preferred.

The compounds of formula (V) in which $R^1$ is RNH- are novel compounds. Accordingly the present invention provides acylated hexahydropyrimidines of formula (Va)

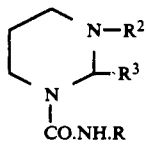

(Va)

where R, $R^2$ and $R^3$ have the meanings given above.

EXAMPLE 1

N-isopropylhexahydropyrimidine

A solution of N-isopropyl-1,3-propanediamine (116 g, 1 M) in isopropyl alcohol (1 l) maintained ca 10° was treated dropwise with 40% aqueous HCHO solution (75 ml, 1 M). After 1 hour the solvents were evaporated under reduced pressure and the residue distilled to give N-isopropylhexahydropyrimidine (100 g, 78%), Bp 65°/20 mbar.

EXAMPLE 2

1-(2,6-Dimethylphenylaminocarbonyl)-3-isopropylhexahydropyrimidine 2,6-Dimethylphenylisocyanate (1.5 g) was added dropwise to a solution of N-isopropylhexahydropyrimidine (1.3 g) in acetonitrile (5 ml) (exothermic). After cooling the title compound was isolated by filtration and recrystallised from acetonitrile (2,5 g, 89%), mp 138°–139° C.

Found: C, 69.90; H. 9.13; N, 15.26%.

$C_{16}H_{25}N_3O$ requires: C, 69.78; H, 9.15; N, 15.26%.

EXAMPLE 3

N-(2,6-Dimethylphenyl)-N'-[3-(isopropylamino)propyl]urea

A solution of 1-(2,6-dimethylphenylaminocarbonyl)-3-isopropylhexahydropyrimidine (1 g) in methanol (5 ml), saturated aqueous sodium metabisulphate (5 ml), and water (5 ml) was stirred at room temperature for 1 hour. HPLC indicated that complete conversion to recainam had taken place. The methanol was evaporated under reduced pressure and the product extracted with dichloromethane. The organic phase was dried and evaporated. The residue was dissolved in isopropanol and treated with excess etherial HCl. The product (recainam HCl), (1 g), obtained by filtration and drying in vacuo, was identical with authentic material (i/r, nmr, hplc).

I claim:

1. A compound of formula

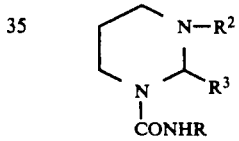

where R is $C_{1-6}$ alkyl or $C_{6-10}$ aryl, wherein the alkyl or aryl group is optionally substituted with one or more groups selected from the group consisting of halogen, hydroxy, lower alkoxy, amino, lower alkylamino, diloweralkylamino, lower acylamino and trifluoromethyl, $R^2$ is lower alkyl and $R^3$ is hydrogen or lower alkyl.

2. A compound of claim 1 which is 1-(2,6-dimethylphenylaminocarbonyl)-3-isopropylhexahydropyrimidine.

* * * * *

UNITED STATES PATENT AND TRADEMARK OFFICE
CERTIFICATE OF CORRECTION

PATENT NO. : 5,010,196
DATED : April 23, 1991
INVENTOR(S) : Robin G. Shepherd

It is certified that error appears in the above—identified patent and that said Letters Patent is hereby corrected as shown below:

Title page item should read

[75] Inventor: Robin G. Shepherd should read

[73] John Wyeth & Brother, Limited

Signed and Sealed this

Twelfth Day of January, 1993

*Attest:*

DOUGLAS B. COMER

*Attesting Officer*     *Acting Commissioner of Patents and Trademarks*